US009046469B2

(12) United States Patent
Kono et al.

(10) Patent No.: US 9,046,469 B2
(45) Date of Patent: Jun. 2, 2015

(54) ULTRASONIC TESTING METHOD

(75) Inventors: Naoyuki Kono, Mito (JP); Atsushi Baba, Tokai (JP); Yoshinori Musha, Hitachiohta (JP)

(73) Assignee: Mitsubishi Hitachi Power Systems, Ltd., Kanagawa (JP)

( * ) Notice: Subject to any disclaimer, the term of this patent is extended or adjusted under 35 U.S.C. 154(b) by 543 days.

(21) Appl. No.: 13/222,523

(22) Filed: Aug. 31, 2011

(65) Prior Publication Data

US 2012/0055251 A1 Mar. 8, 2012

(30) Foreign Application Priority Data

Sep. 2, 2010 (JP) ................................. 2010-196989

(51) Int. Cl.
*G01N 29/07* (2006.01)
*G01B 17/02* (2006.01)

(52) U.S. Cl.
CPC ................ *G01N 29/07* (2013.01); *G01B 17/02* (2013.01); *G01N 2291/02854* (2013.01); *G01N 2291/0234* (2013.01); *G01N 2291/102* (2013.01)

(58) Field of Classification Search
CPC ............. G01B 17/02; G01N 2291/102; G01N 2291/02854; G01N 2291/0234
USPC ........... 73/597, 598, 600, 602, 625, 626, 628, 73/641
See application file for complete search history.

(56) References Cited

U.S. PATENT DOCUMENTS

| 4,375,165 | A | * | 3/1983 | de Sterke ......................... 73/622 |
| 4,481,822 | A | * | 11/1984 | Kubota et al. ................... 73/625 |
| 4,524,622 | A | * | 6/1985 | Suzuki et al. ................... 73/620 |
| 5,042,305 | A | * | 8/1991 | Takishita ........................ 73/625 |
| 5,111,696 | A | * | 5/1992 | Lund et al. ..................... 73/627 |
| 5,307,680 | A | * | 5/1994 | Drescher-Krasicka ......... 73/606 |
| 5,549,003 | A | * | 8/1996 | Drescher-Krasicka ......... 73/606 |
| 5,955,671 | A |  | 9/1999 | Gilmore et al. |
| 8,079,266 | B2 | * | 12/2011 | Nichiforenco et al. ......... 73/643 |
| 8,175,820 | B2 | * | 5/2012 | Hatanaka et al. ............... 702/39 |
| 8,225,668 | B2 | * | 7/2012 | Yabushita et al. .............. 73/624 |
| 8,490,490 | B2 | * | 7/2013 | Yamano ......................... 73/602 |

FOREIGN PATENT DOCUMENTS

JP 2000-338092 A 12/2000

OTHER PUBLICATIONS

European Office Action dated Jan. 15, 2014 (7 pages).
Every et al. "Angular Spectrum Method and Ray Algorithm for the Acoustic Field of a Focusing Transducer in an Anisotropic Solid" IEEE Transactions on Ultrasonics, Ferroelectrics, and Frequency Control, vol. 49, No. 3, Mar. 1, 2002, pp. 307-318.
Hsu et al. "Simultaneous determination of ultrasonic velocity, plate thickness and wedge angle using one-sided contact measurements" NDT & E International , vol. 27, No. 2, Apr. 1, 1994, pp. 75-82.

* cited by examiner

*Primary Examiner* — J M Saint Surin
(74) *Attorney, Agent, or Firm* — Crowell & Moring LLP (57) ABSTRACT

An ultrasonic testing method is provided to measure a thickness of an object in a simple and highly accurate manner when crystal grains that form a metal solidification structure of a directionally-solidified material cast or the like have a statistical variation.
An ultrasonic probe 102 causes a longitudinal ultrasonic wave to be incident on a test object 101 in a direction perpendicular to a surface 101A of the test object 101. As a velocity of the longitudinal ultrasonic wave, the average of velocities of longitudinal ultrasonic waves propagating in directions of crystal orientations <100>, <110>, and <210> is used. The thickness of the test object 101 is measured on the basis of the velocity of the ultrasonic wave and a time period for the propagation of the ultrasonic wave.

2 Claims, 12 Drawing Sheets

ANGLE θ1 FORMED BETWEEN <100> AND DIRECTION
OF PROPAGATION OF ULTRASONIC WAVE

<100>
TEST
BODY

FIG. 6A

<110>
TEST
BODY

FIG. 6B

<210>
TEST
BODY

ANGLE FORMED BETWEEN <100> AND DIRECTION OF PROPAGATION OF ULTRASONIC WAVE

ULTRASONIC TESTING METHOD

BACKGROUND OF THE INVENTION

1. Field of the Invention

The present invention relates to an ultrasonic testing method. The invention particularly relates to an ultrasonic testing method that is suitable for measuring a dimension such as a thickness of a cast having acoustic anisotropy, such as a directionally-solidified material, a single-crystalline material or the like.

2. Description of the Related Art

Traditionally, an ultrasonic testing method using a reflected longitudinal wave or a reflected transverse wave has been used for measurement of a dimension such as the thickness of metal or the like. Such a method is as follows. A pulsed longitudinal wave or a pulsed transverse wave propagates from a front surface of a test object to the inside of the test object. A wave that is reflected from a bottom surface of the test object is received. A time period for propagation of the reflected wave, or the difference between time periods for propagation of multiply-reflected waves, is measured. A distance by which the ultrasonic wave propagates from the bottom surface to the front surface is calculated by multiplying the time period in which the ultrasonic wave propagates from the bottom surface to the front surface by the acoustic velocity. In this manner, the thickness of the test object is calculated.

A velocity of an ultrasonic wave that propagates in a metal material (such as rolled steel or a casting material) that is processed and thereby has a homogeneous crystalline structure is almost constant regardless of a direction in which the ultrasonic wave propagates. The material that has this characteristic is called an isotropic material. In the aforementioned method, the thickness of the isotropic material can be measured with high accuracy.

A cast is constituted by a coarse solidification structure (crystal grains) formed in a process of cooling molten metal. It is generally known that the solidification structure has a characteristic (acoustical anisotropy) in which acoustic properties such as a velocity and attenuation vary with a direction in which an ultrasonic wave propagates.

For example, in an austenitic material such as stainless steel or a Ni-based alloy, crystal grains form a cubic single crystal. In a cooling process, the material is solidified while a crystal orientation of the material is <100> (<100> is a notation that is treated equivalently to [100], [010], [001] and the like). The crystal orientation <100> is called a crystal growth direction. The solidification structure is constituted by a plurality of crystal grains. Thus, the acoustic characteristics of the cast depend on the statistic of characteristics of the plurality of crystal grains. The crystal growth direction is a direction that is parallel to or nearly parallel to the crystal orientation <100>, while the crystal growth direction varies in a range of approximately 15 degrees. In addition, it is known that crystal orientations (of crystal grains) that are perpendicular to the crystal growth direction are random.

When a thickness of a test object (such as a cast) constituted by a coarse solidification structure is to be measured, especially, when a thickness of the test object is to be measured in a direction perpendicular to the crystal growth direction, crystal orientations are random with respect to the direction in which the thickness is measured. Thus, a velocity of an ultrasonic wave varies due to acoustic anisotropy, depending on the direction in which the ultrasonic wave propagates. Therefore, it is difficult to measure the thickness of the test object with high accuracy.

Another method is known in which an effective acoustic velocity is measured in advance using a calibration test body having the same crystal orientations as those of the test object and the thickness of the test object is measured. However, since crystal orientations that are perpendicular to the crystal growth direction <100> are random, it is difficult to reproduce the acoustic velocity in the test object by use of the calibration test body.

In order to perform the measurement with high accuracy, it is necessary to measure crystal orientations of crystal grains forming a solidification structure in advance. Thus, there is a problem that a simple measurement cannot be performed.

In addition, as an ultrasonic testing method for measuring an anisotropic material for which the testing method for an isotropic material is not directly effective, a method in which a transverse ultrasonic wave that has a polarization (or vibration direction) in the same direction as the crystal growth direction of the test object is incident on the test object (refer to, for example, JP-2000-338092-A).

SUMMARY OF THE INVENTION

However, a solidification structure such as a cast has a statistical variation in a crystal growth direction of crystal grains. Thus, in order to match the polarization (vibration direction) of the transverse ultrasonic wave with the crystal growth direction <100> like as JP-2000-338092-A, it is necessary to measure in advance the crystal growth direction of the crystal grains (forming the test object) by another method such as a macro observation or the like. Even when the crystal growth direction of crystal grains that are located in a region in which the thickness of the test object is measured, is measured in advance, the crystal growth direction does not necessarily exist on the surface of the test object. Thus, it is difficult to cause a transverse wave having a polarization (or vibration direction) in the crystal growth direction to propagate.

When the test object has acoustic anisotropy and a statistical variation in the crystal growth direction of the crystal grains forming the solidification structure that is the cause of acoustic anisotropy, it is necessary to measure the direction of extension of the structure in advance in order to measure the thickness of the test object with high accuracy. Thus, there is a problem that it is difficult to measure the thickness in a simple and highly accurate manner.

An object of the present invention is to provide an ultrasonic testing method for measuring a thickness in a simple and highly accurate manner when crystal grains of an object such as a directionally-solidified material cast form a metal solidification structure and have a statistical variation.

(1) In order to accomplish the aforementioned object, according to the present invention, an ultrasonic testing method includes the steps of: causing a longitudinal ultrasonic wave to be incident on a test object that has acoustic anisotropy and is constituted by a crystal structure, in a direction perpendicular to a surface of the test object; and measuring a thickness of the test object on the basis of a velocity of the longitudinal ultrasonic wave propagating in the test object and a time period for the propagation of the longitudinal ultrasonic wave, while using, as the velocity of the longitudinal ultrasonic wave, the average of velocities of longitudinal waves propagating in directions of crystal orientations <100>, <110>, and <210>.

In the ultrasonic testing method, when the thickness is to be measured in a direction perpendicular to a crystal growth direction, the average of acoustic velocities of waves that propagate in the directions parallel to the crystal orientations of crystal grains forming a solidification structure can be approximately obtained using the average of the velocities of the ultrasonic waves propagating in the directions parallel to the three crystal orientations <100>, <110> and <210> of the crystal grains. In this case, the crystal orientations are perpendicular to the crystal growth direction and random for the crystal grains. Even when crystal grains of an object such as a directionally-solidified material cast form a metal solidification structure and have a statistical variation, it is possible to measure the thickness of the test object on the basis of the time period for the propagation of the ultrasonic wave in the test object, the average acoustic velocity, and a distance that the longitudinal ultrasonic wave propagates in the test object. Thus, even when the crystal grains of the object such as the directionally-solidified material cast or the like form the metal solidification structure and have the statistical variation, it is possible to measure the thickness of the test object in a simple and highly accurate manner.

(2) In order to accomplish the aforementioned object, according to the present invention, an ultrasonic testing method includes the steps of: causing a transverse ultrasonic wave to be incident on a test object that has acoustic anisotropy and is constituted by a crystal structure, in a direction perpendicular to a surface of the test object; and measuring a thickness of the test object on the basis of a velocity of the transverse ultrasonic wave propagating in the test object and a time period for the propagation of the transverse ultrasonic wave, while using, as the time period for the propagation of the transverse ultrasonic wave, a time period for propagation of a transverse wave component that propagates in the test object for the shortest time period, among a plurality of transverse wave components that are obtained by dividing the transverse ultrasonic wave and have polarizations in the different directions (vibration direction) due to the acoustic anisotropy.

In the ultrasonic testing method, the transverse ultrasonic wave propagates in the test object that has crystal grains with the acoustic anisotropy, and the transverse ultrasonic wave is divided into the plurality of transverse wave components that have polarizations (or vibration direction) in the different directions due to the acoustic anisotropy. The time period for the propagation of the transverse wave component that propagates at the highest acoustic velocity and is hardly affected by the acoustic anisotropy, is focused. When the thickness is to be measured in a direction perpendicular to a crystal growth direction, it is possible to measure the average time period for propagation by focusing the time period for the propagation of a divided transverse wave component that is hardly affected by statistical randomness of crystal orientations that are random for crystal grains and perpendicular to the crystal growth direction. Thus, even when crystal grains of an object such as a directionally-solidified material cast form a metal solidification structure and have a statistical variation, it is possible to measure the thickness of the test object on the basis of the average time period for the propagation of the transverse ultrasonic waves in the test object, an ultrasonic velocity of the divided transverse ultrasonic wave component propagating at the highest velocity, and a distance that the transverse ultrasonic wave propagates in the test object. As a result, even when the crystal grains of the object such as the directionally-solidified material cast form the metal solidification structure and have the statistical variation, it is possible to measure the thickness of the test object in a simple and highly accurate manner.

(3) In the aforementioned item (2), it is preferable that as the velocity of the transverse ultrasonic wave, a velocity of a transverse ultrasonic wave is used which is higher than that of the other transverse ultrasonic wave, the transverse ultrasonic wave being among transverse ultrasonic waves that propagate in a direction of a crystal orientation <100> and have polarizations in two directions.

(4) In order to accomplish the aforementioned object, according to the present invention, an ultrasonic testing method includes the steps of: arranging an ultrasonic probe for transmission and an ultrasonic probe for reception in a direction parallel to a crystal growth direction so that the ultrasonic probes face a test object that has acoustic anisotropy and is constituted by a crystal structure; causing a longitudinal ultrasonic wave to be incident on the test object in a direction oblique to a surface of the test object so that the longitudinal ultrasonic wave propagates in the test object; and measuring a thickness of the test object on the basis of a velocity of the longitudinal ultrasonic wave propagating in the test object and a time period for the propagation of the longitudinal ultrasonic wave.

In the ultrasonic testing method, when the thickness of the test object that has crystal grains with the acoustic anisotropy is to be measured in a direction perpendicular to the crystal growth direction by causing the longitudinal ultrasonic wave to propagate in a direction oblique to a surface of the test object, it is possible to measure the average time period for propagation by focusing a time period for propagation of the ultrasonic wave that propagates in the oblique direction and is hardly affected by statistical randomness of crystal orientations that are random for crystal grains and perpendicular to the crystal growth direction. Thus, even when crystal grains of an object such as a directionally-solidified material cast form a metal solidification structure and have a statistical variation, it is possible to measure the thickness of the test object on the basis of the average time period for propagation of the ultrasonic wave in the test object, a velocity of the longitudinal ultrasonic wave and a distance that the longitudinal ultrasonic wave propagates in the test object. As a result, even when the crystal grains of the object such as the directionally-solidified material cast form the metal solidification structure and have the statistical variation, it is possible to measure the thickness of the test object in a simple and highly accurate manner.

(5) In the aforementioned item (4), it is preferable that as the velocity of the longitudinal ultrasonic wave, the average of the maximum and minimum velocities of longitudinal ultrasonic waves is used, the longitudinal ultrasonic waves propagating in a direction of a crystal orientation <110>.

According to the present invention, even when crystal grains of an object such as a directionally-solidified material cast form a metal solidification structure and have a statistical variation, it is possible to measure a thickness of the test object in a simple and highly accurate manner.

DESCRIPTION OF THE PREFERRED EMBODIMENTS

Details of an ultrasonic testing method according to a first embodiment of the present invention are described below with reference to FIGS. 1 to 8.

First, the configuration of an ultrasonic testing device that is used for the ultrasonic testing method according to the present embodiment is described with reference to FIG. 1.

Figure 1:
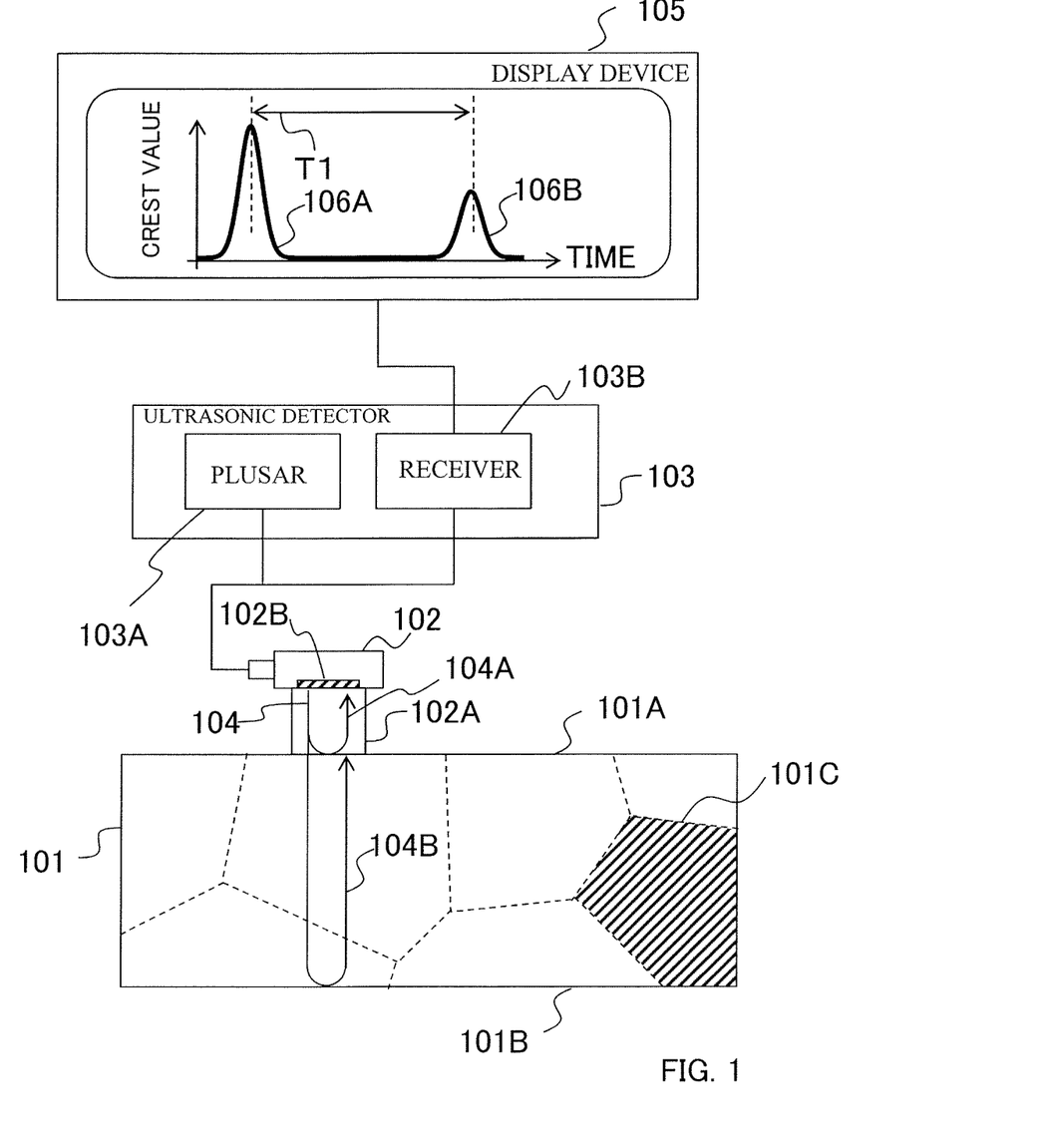
FIG. 1 is a diagram illustrating the configuration of an ultrasonic testing device that is used for an ultrasonic testing method according to a first embodiment of the present invention.

FIG. 1 is a diagram illustrating the configuration of the ultrasonic testing device that is used for the ultrasonic testing method according to the first embodiment of the present invention.

A vertical incidence type longitudinal ultrasonic wave probe 102 is in contact with a test object 101 through a buffer (shoe) 102A. The test object 101 is made of a directionally-solidified material. The buffer 102A is a block made of a synthetic resin such as polystyrene and is used to receive a wave reflected from a top surface 101A of the test object 101. The vertical incidence type longitudinal ultrasonic wave probe 102 and the buffer 102A are in contact with each other through a couplant. The buffer 102A and the test object 101 are in contact with each other through a couplant. If the top surface 101A of the test object 101 is not processed so as to be flat, the buffer 102A may be processed so as to have a curved shape in order to improve the contact with the test object 101, for example.

The vertical incidence type longitudinal ultrasonic wave probe 102 transmits and receives an ultrasonic wave and has a piezoelectric transducer 102B. An ultrasonic detector 103 has a pulsar 103A and a receiver 103B.

The pulsar 103A of the ultrasonic detector 103 supplies voltage to the vertical incidence type longitudinal ultrasonic wave probe 102. The piezoelectric transducer 102B that is included in the vertical incidence type longitudinal ultrasonic wave probe 102 converts an electric signal into a vibration. The vibration causes a longitudinal ultrasonic wave 104 to be generated in the test object 101. The ultrasonic wave 104 is transmitted in a direction perpendicular to the top surface 101A of the test object 101 so that a wave 104A reflected on the top surface 101A of the test object 101 and a wave 104B reflected on a bottom surface 101B of the test object 101 are generated.

The reflected ultrasonic waves 104A and 104B are converted from vibrations to electric signals by the piezoelectric transducer 102B of the vertical incidence type longitudinal ultrasonic wave probe 102. The converted electric signals are received by the receiver 103B of the ultrasonic detector 103 and displayed as waveform signals 106A and 106B by a display device 105. The waveform signal 106A is a waveform of the wave 104A reflected from the top surface 101A of the test object 101, while the waveform signal 106B is a waveform of the wave 104B reflected from the bottom surface 101B of the test object 101. A time difference T1 between a time period for propagation of the wave 104A and a time period for propagation of the wave 104B in the test object 101 is measured based on the waveform signals 106A and 106B. The thickness of the test object is evaluated by multiplying the time difference T1 by a velocity of the ultrasonic wave.

Details of the test object 101 that is an object to be tested in the ultrasonic testing method according to the present embodiment, are described with reference to FIGS. 2, 3A and 3B.

Figure 2:
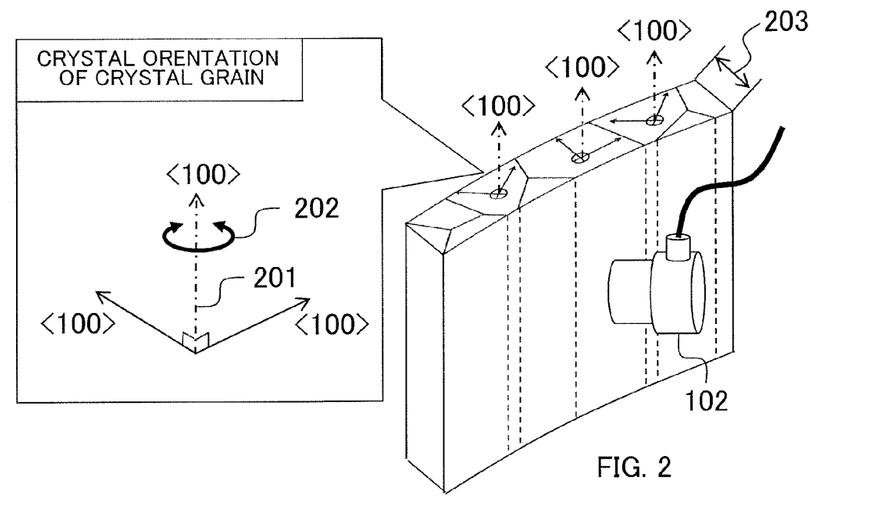
FIG. 2 is a diagram illustrating a test object that is an object to be tested in the ultrasonic testing method according to the first embodiment of the present invention.
Figure 3:
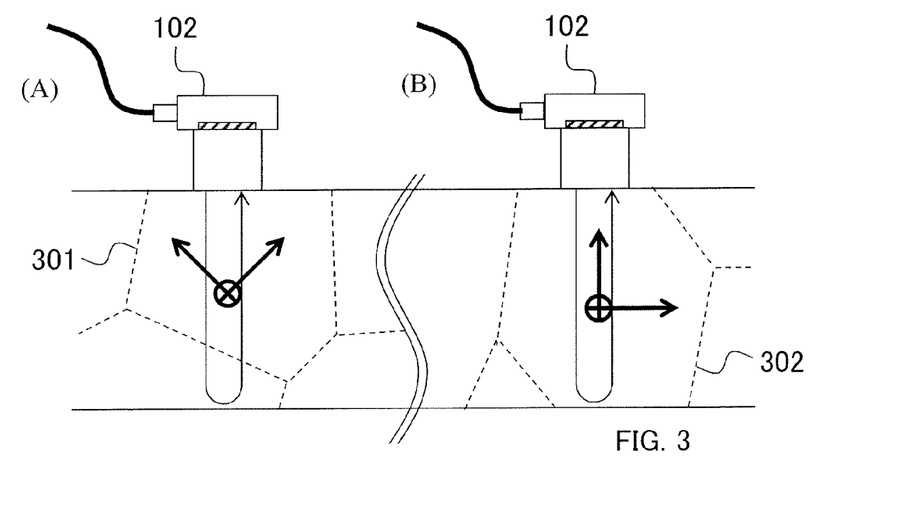
FIG. 3 is diagram illustrating the test object that is the object to be tested in the ultrasonic testing method according to the first embodiment of the present invention.

FIGS. 2, 3A and 3B are diagrams illustrating the test object that is the object to be tested in the ultrasonic testing method according to the first embodiment of the present invention.

As illustrated in FIG. 1, the directionally-solidified material that is the test object 101 is a cast called a directionally-solidified material, and is a polycrystalline body constituted by a plurality of crystal grains 101C whose crystal orientations are the same specific orientation.

The specific crystal orientation is a crystal orientation in which the cast is grown in a cooling process. When the test object is cubic-system metal such as stainless steel or a Ni-based alloy, the metal has a characteristic in which a crystal growth direction 201 is a crystal orientation <100> (direction [010] illustrated in an enlarged view of FIG. 2) as illustrated in FIG. 2. However, crystal orientations (directions [001] and [100] illustrated in the enlarged view of FIG. 2) that are perpendicular to the crystal growth direction 201 are random.

The crystal grains that form the directionally-solidified material can be approximately treated as a model in which the crystal growth direction 201 is the direction <100> and an angle 202 of a rotation around the crystal growth direction 201 is random.

As illustrated in FIG. 2, in the directionally-solidified material, when a thickness 203 of the test object in the direction perpendicular to the crystal growth direction is measured, an angle that is formed between the direction of propagation of the ultrasonic wave and a crystal grain varies with a region in which the thickness is measured, due to randomness of the crystal orientations perpendicular to the crystal growth direction. For example, in a crystal grain 301 illustrated in FIG. 3 (A), the crystal orientation <100> (directions [100] and [001] in an example illustrated in the enlarged view of FIG. 2) is inclined at an angle of approximately 45 degrees with respect to the direction in which the ultrasonic wave propagates. In a crystal grain 302 illustrated in FIG. 3 (B), the ultrasonic wave propagates in a direction that is nearly parallel to the crystal orientation <100> (direction or [001] in the example illustrated in the enlarged view of FIG. 2).

Figure 4A:
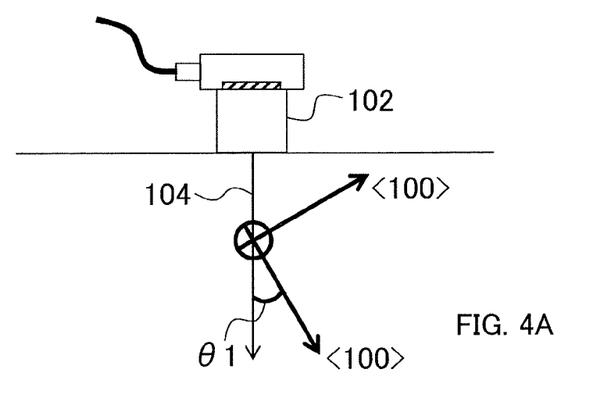
FIGS. 4A and 4B are diagrams explaining changes in a velocity of an ultrasonic wave propagating in a directionally-solidified material.
Figure 4B:
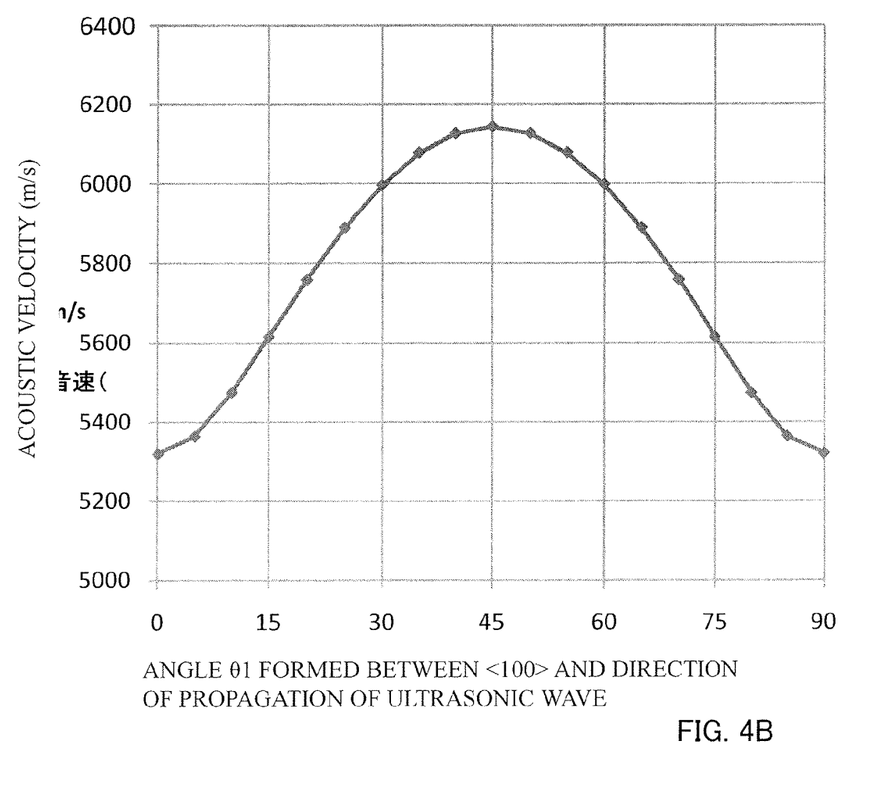

Changes in the velocity of the ultrasonic wave propagating in the directionally-solidified material are described with reference to FIGS. 4A and 4B. FIGS. 4A and 4B are diagrams explaining the changes in the velocity of the ultrasonic wave propagating in the directionally-solidified material. In FIGS. 4A and 4B, reference numerals that are the same as those in FIG. 1 indicate the same parts.

FIG. 4A is the diagram illustrating an angle $\theta 1$ formed between a direction 104 of propagation of the ultrasonic wave and the crystal orientation <100>.

FIG. 4B illustrates theoretical values of a velocity of a longitudinal ultrasonic wave propagating in nickel base metal as an example of the changes in the velocity of the ultrasonic wave propagating in the direction 104 that forms the angle $\theta 1$ with the crystal orientation <100>.

It is apparent that when the direction of the propagation of the ultrasonic wave is parallel to the crystal orientation <100> (direction [100] or [001] in the example illustrated in the enlarged view of FIG. 2) (or when the angle $\theta 1$ is 0 degrees), the velocity of the ultrasonic wave is the lowest and approximately 5300 m/s. In addition, it is apparent that when the direction of the propagation of the ultrasonic wave and the crystal orientation <100> (direction [100] or [001] in the example illustrated in the enlarged view of FIG. 2) forms an angle of 45 degrees, the velocity of the ultrasonic wave is the highest and approximately 6100 m/s. In the directionally-solidified material, a crystal orientation of a crystal grain at which the thickness is measured is random. Thus, the velocity of the ultrasonic wave that propagates in the crystal grain cannot be fixed.

In order to measure the thickness of the test object by use of the ultrasonic wave, the velocity of the ultrasonic wave is multiplied by the time period for the propagation of the ultrasonic wave. Thus, if the velocity cannot be determined, the thickness cannot be calculated.

In the present embodiment, the thickness of the test object is measured using the average of acoustic velocities. As a conventional method for calculating the average of acoustic velocities, there is a method for evaluating the average of acoustic velocities using a calibration test body that is formed by simulating the test object. However, the test object has the randomness. Thus, in order to obtain a statistically significant velocity value, it is necessary to measure a plurality of locations in a plurality of calibration test bodies.

Next, the average of acoustic velocities, which is used in the ultrasonic testing method according to the present embodiment, is described with reference to FIGS. 5A and 5B.

Figure 5A:
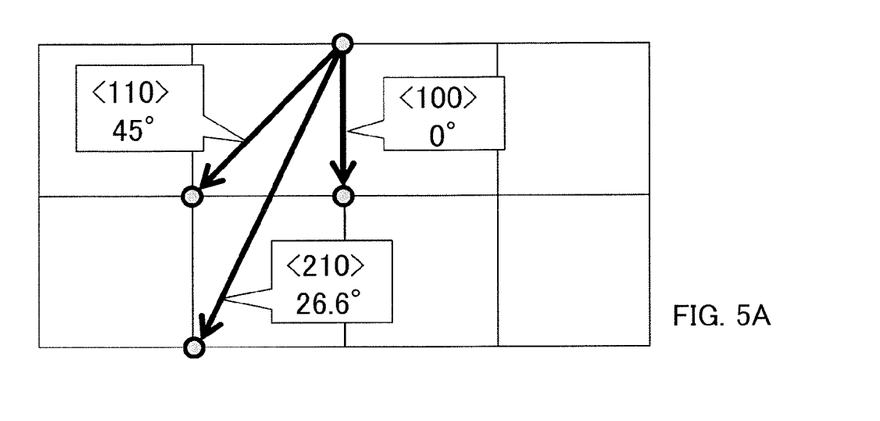
FIGS. 5A and 5B are diagrams explaining an average acoustic velocity that is used in the ultrasonic testing method according to the first embodiment of the present invention.
Figure 5B:
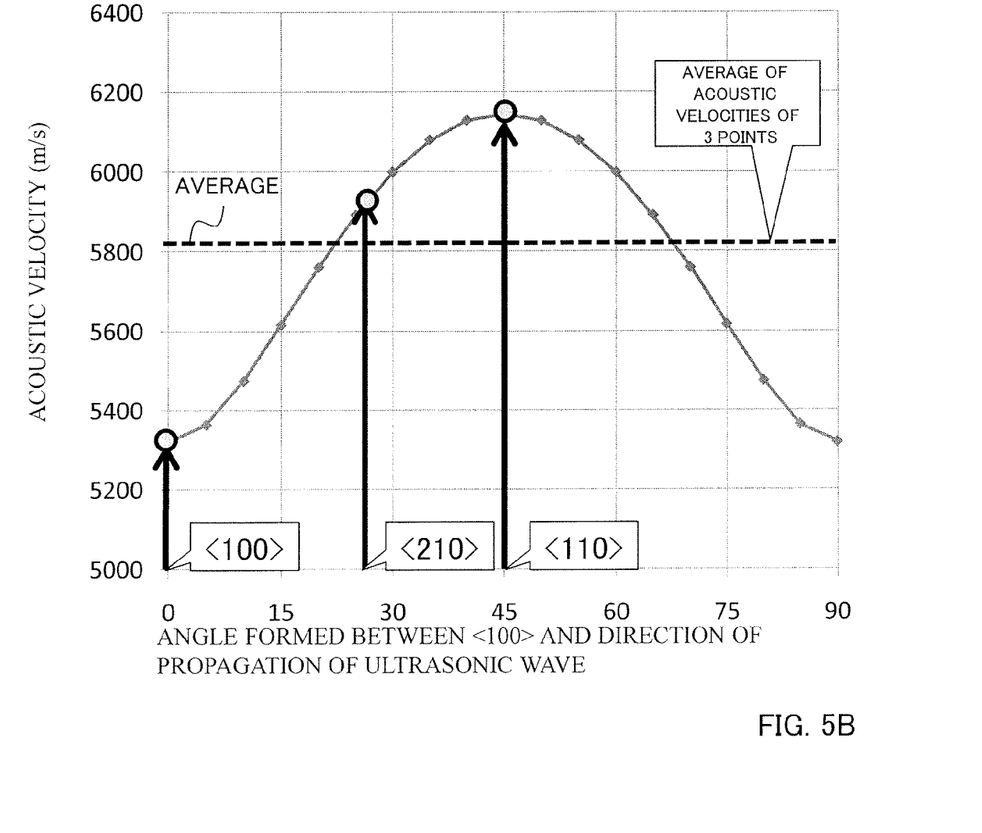

FIGS. 5A and 5B are diagrams explaining the average of acoustic velocities which is used in the ultrasonic testing method according to the first embodiment of the present invention.

As illustrated in FIG. 5A, in order to calculate the average of acoustic velocities, three directions that are a direction <100>, a direction <110> and a direction <210> are considered as crystal orientations. Then, velocities of ultrasonic waves that propagate in the three directions are calculated.

FIG. 5B illustrates the velocities of the longitudinal ultrasonic waves that propagate in the three directions <100>, <110> and <210>. In the present embodiment, the average of the velocities of the longitudinal ultrasonic waves propagating in the three directions is used as an average acoustic velocity.

When a thickness of the test object is to be measured in a direction perpendicular to the crystal growth direction, the average of velocities of ultrasonic waves that propagate in directions parallel to the crystal orientations <100>, <110> and <210>, is used. The crystal orientation s are randomly directed for the crystal grains and perpendicular to the crystal growth direction. Thereby, the average acoustic velocity of waves that propagate in the directions parallel to the crystal orientations of crystal grains forming a solidification structure, can be approximately obtained. Even when the crystal grains of the test object such as a directionally-solidified material cast form a metal solidification structure and have a statistical variation, it is possible to measure the thickness of the test object on the basis of the time period for the propagation of the ultrasonic wave in the test object, the average acoustic velocity, and a distance that the longitudinal ultrasonic wave propagates in the test object.

When the direction of the propagation of the ultrasonic wave is parallel to the direction <100> (or when the angle $\theta 1$ is 0 degrees), the velocity of the ultrasonic wave in the direction <100> is approximately 5300 m/s. When the direction of the propagation of the ultrasonic wave is inclined at an angle of 45 degrees with respect to the direction <100>, the velocity of the ultrasonic wave in the direction <110> is approximately 6100 m/s. When the direction of the propagation of the ultrasonic wave is inclined at an angle of 22.6 degrees with respect to the direction <100>, the velocity of the ultrasonic wave in the direction <210> is approximately 5900 m/s. The average of the velocities is approximately 5800 m/s.

When the average acoustic velocity is used, the randomness of the orientations perpendicular to the crystal growth direction is replaced with the average value, an error is thereby reduced and an acoustic velocity is specified, so that the thickness of the test object can be evaluated. In addition, the average acoustic velocity is calculated on the basis of the velocities of the ultrasonic waves propagating in the specific crystal orientations. Thus, it is sufficient if a calibration test body that has the known crystal orientations is formed. Therefore, it is not necessary to prepare a plurality of calibration test bodies formed by simulating a crystal structure of the directionally-solidified material. In addition, a calibration can be performed in a simple manner.

As a method for calculating the average acoustic velocity, the average of velocities of longitudinal ultrasonic waves that propagate in the two directions <100> and <110> is calculated. In this case, the average acoustic velocity is calculated from the maximum and minimum of the velocities and is approximately 5700 m/s. As illustrated in FIG. 5B, changes in the velocity of the ultrasonic wave that propagates in directions forming angles of 0 degrees to 45 degrees with respect to the direction <100>, form a convex compared with a line that connects the velocity of the ultrasonic wave propagating in the direction forming the angle of 0 degrees with respect to the direction <100> to the velocity of the ultrasonic wave propagating in the direction forming the angle of 45 degrees with respect to the direction <100>. Thus, the average of the velocities of the longitudinal ultrasonic waves propagating in the two directions <100> and <110> is slightly smaller than the average of the velocities of the ultrasonic waves propagating in the directions that form the angles of 0 degrees to 45 degrees with respect to the direction <100>. The average of velocities of longitudinal ultrasonic waves that propagate in the three directions <100>, <110> and <210> is approximately 5800 m/s. The thicknesses of several types of test bodies are measured using the aforementioned average acoustic velocity and relatively closely match each other. Thus, the average of the velocities of the longitudinal ultrasonic waves propagating in the three directions is used as the average acoustic velocity so that an error can be reduced.

Next, the configurations of calibration test bodies that are used in the ultrasonic testing method according to the present embodiment are described with reference to FIGS. 6A to 6D.

FIGS. 6A to 6D are diagrams illustrating the calibration test bodies that are used in the ultrasonic testing method according to the first embodiment of the present invention.

A material that is same as or similar to the directionally-solidified material is used as a material of the calibration test bodies that are used in the present embodiment. The test bodies are formed as single-crystalline materials.

As the calibration test bodies, the following three types of calibration test bodies are used: a test body 600A (illustrated in FIG. 6A) whose crystal orientation is the direction <100>; a test body 600B (illustrated in FIG. 6B) whose crystal orientation is the direction <110>; and test body 600C (illustrated in FIG. 6C) whose crystal orientation is the direction <210>.

Figure 6A:
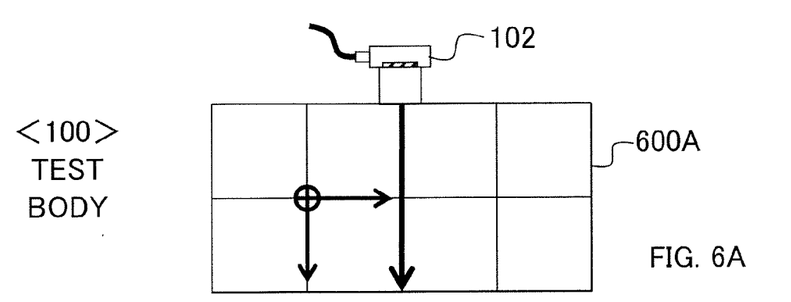
FIGS. 6A to 6D are diagrams illustrating calibration test bodies that are used in the ultrasonic testing method according to the first embodiment of the present invention.
Figure 6B:
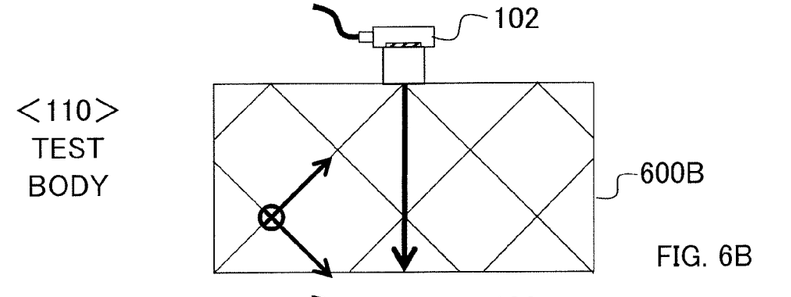
Figure 6C:
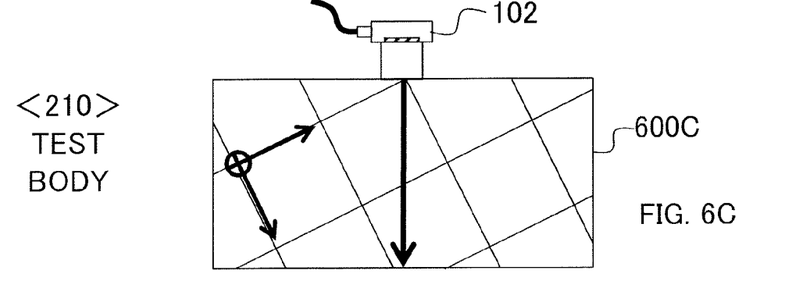
Figure 6D:
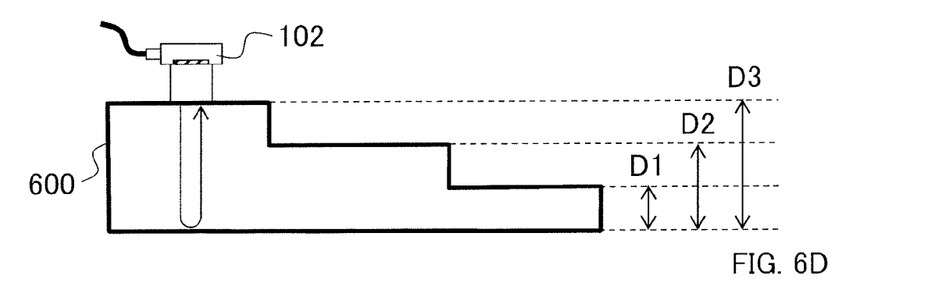

The test bodies are processed so that the test bodies each includes parts (D1, D2 and D3) having different thicknesses, like a step-like test body illustrated in FIG. 6D. The step-like test bodies 600 are prepared and have the different crystal orientations illustrated in FIGS. 6A to 6C, respectively.

As illustrated in FIG. 6D, velocities of longitudinal ultrasonic waves that propagate in the parts (D1, D2 and D3) that are included in any of the step-like test bodies 600 and have the different thicknesses, are calculated using the ultrasonic wave probe 102. The average of the velocities is treated as an acoustic velocity for the crystal orientation of the test body 600. In the same manner, velocities of longitudinal ultrasonic waves that propagate in the parts (D1, D2 and D3) that are included in each of the other two step-like test bodies 600 and having the different thicknesses are calculated. Then, the average of the calculated three acoustic velocities is calculated as the average acoustic velocity. The thickness of the test object can be calculated by multiplying the average acoustic velocity by the time period for the propagation of the ultrasonic wave propagating in the test object.

Next, a method for calculating the time period for the propagation in the ultrasonic testing method according to the present embodiment is described with reference to FIG. 7.

Figure 7:
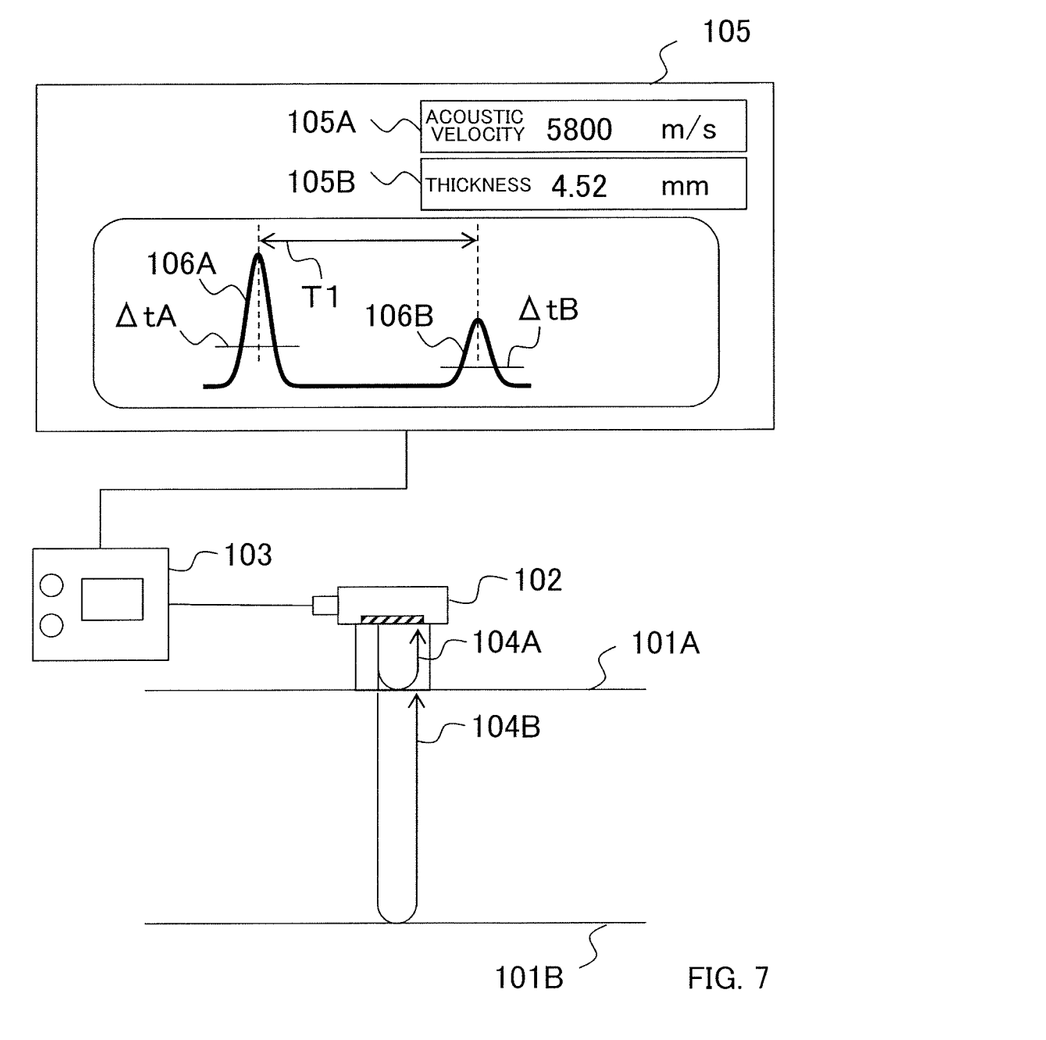
FIG. 7 is a diagram explaining a method for calculating a time period for propagation in the ultrasonic testing method according to the first embodiment of the present invention.

FIG. 7 is a diagram explaining the method for calculating the time period for the propagation in the ultrasonic testing method according to the first embodiment of the present invention.

In order to measure, from the received waveforms 106A and 106B, the time period for the propagation of the ultrasonic wave in the test object, a time gate ΔtA is set for the wave 106A reflected from the top surface 101A of the test object, and a time gate ΔtB is set for the wave 106B reflected from the bottom surface 101B of the test object as illustrated in FIG. 7, for example. Among signals within the time gate ΔtA, a signal having the maximum intensity is selected. Among signals within the time gate ΔtB, a signal having the maximum intensity is selected. Then, the time difference between time points of the selected signals is calculated as the time period T1 for the propagation.

The average acoustic velocity that has been measured using the calibration test bodies as illustrated in FIGS. 6A to 6D is set in the display device 105. The average acoustic velocity is displayed on a display section 105A of the display device 105. In addition, the thickness that is calculated from the time period T1 for the propagation is displayed on a display section 105B of the display device 105.

Figure 8:
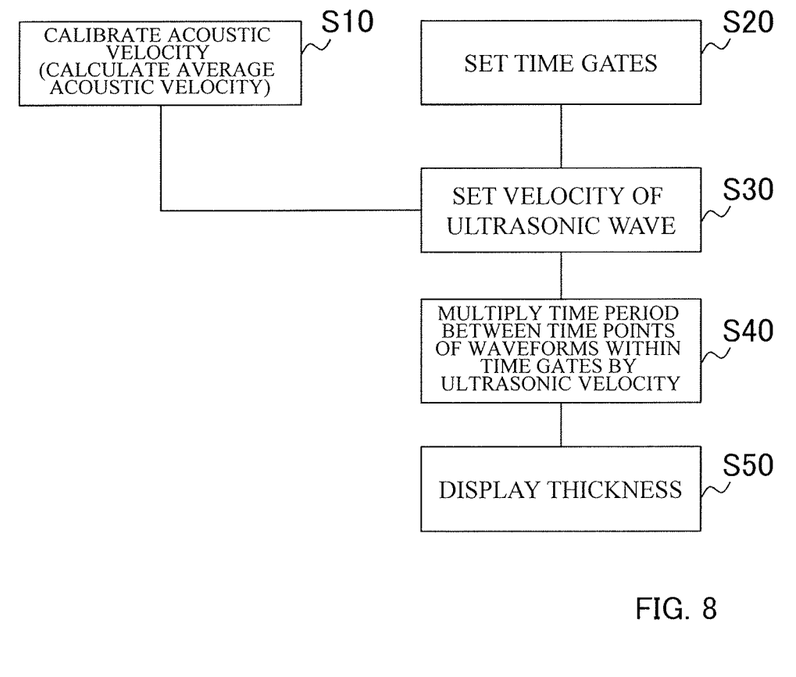
FIG. 8 is a flowchart of procedures of the ultrasonic testing method according to the first embodiment of the present invention.

Next, procedures of the ultrasonic testing method according to the present embodiment are described with reference to FIG. 8. FIG. 8 is a flowchart of the procedures of the ultrasonic testing method according to the first embodiment of the present invention.

First, the average acoustic velocity is calculated using the three types of the calibration test bodies that have the crystal orientations <100>, <110> and <210>, respectively (in step S10).

The time gates are set in the ultrasonic detector (in step S20). The average acoustic velocity that is calculated in step S10 is set in the ultrasonic detector (in step S30).

The time period T1 (for the propagation) that is between the time points of the waveforms within the time gates is multiplied by the average acoustic velocity, and the value obtained by the multiplication is divided by 2 so that the thickness is calculated (the thickness=time period for the propagation×the average acoustic velocity/2) (in step S40). The calculated thickness of the test object is displayed (in step S50).

In the aforementioned equation, the reason that the value obtained by the multiplication is divided by 2 is that the distance (=thickness) corresponding to a one-way propagation path (not a both-way propagation path) is calculated.

According to the present embodiment, even when the test object is the directionally-solidified material and crystal orientations that are perpendicular to the crystal growth direction are random, the thickness of the test object can be measured using the average of the velocities of the longitudinal ultrasonic waves as described above.

Next, details of an ultrasonic testing method according to a second embodiment of the present invention are described with reference to FIGS. 9 to 11.

First, the configuration of an ultrasonic testing device that is used for the ultrasonic testing method according to the present embodiment is described with reference to FIG. 9.

Figure 9:
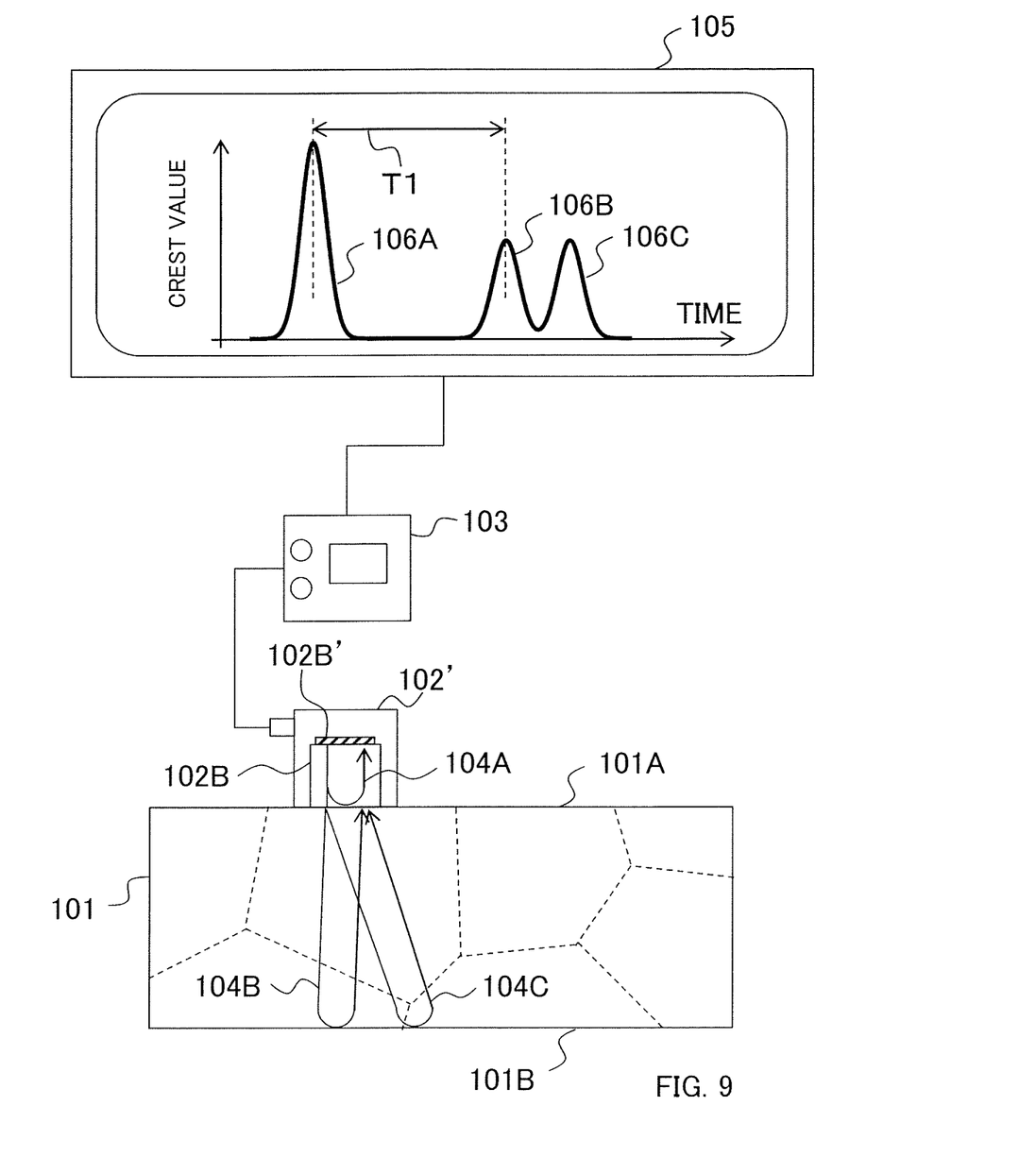
FIG. 9 is a diagram illustrating the configuration of an ultrasonic testing device that is used for an ultrasonic testing method according to a second embodiment of the present invention.

FIG. 9 is a diagram illustrating the configuration of the ultrasonic testing device that is used for the ultrasonic testing method according to the second embodiment of the present invention. In FIG. 9, reference numerals that are the same as those in FIG. 1 indicate the same parts.

In the present embodiment, a vertical incidence type transverse wave probe 102' is used. Other configurations are the same as those in FIG. 1. A buffer 102B is provided to receive a wave reflected from the top surface 101A of the test object. The vertical incidence type transverse wave probe 102' has a piezoelectric transducer 102B' that provides a vibration in a shearing direction.

Next, a measurement principle of the ultrasonic testing method according to the present embodiment is described with reference to FIGS. 10 and 11.

Figure 10:
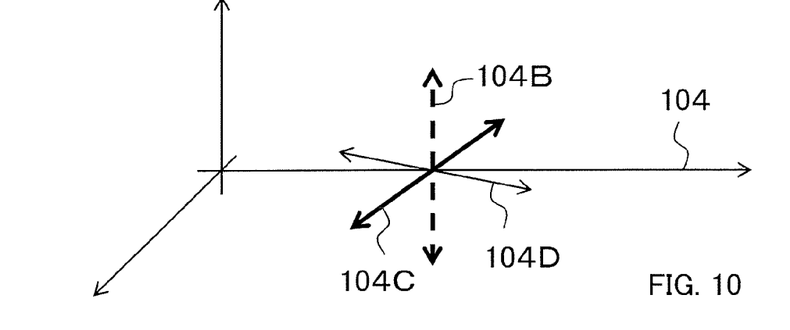
FIG. 10 is a diagram illustrating a measurement principle of the ultrasonic testing method according to the second embodiment of the present invention.
Figure 11:
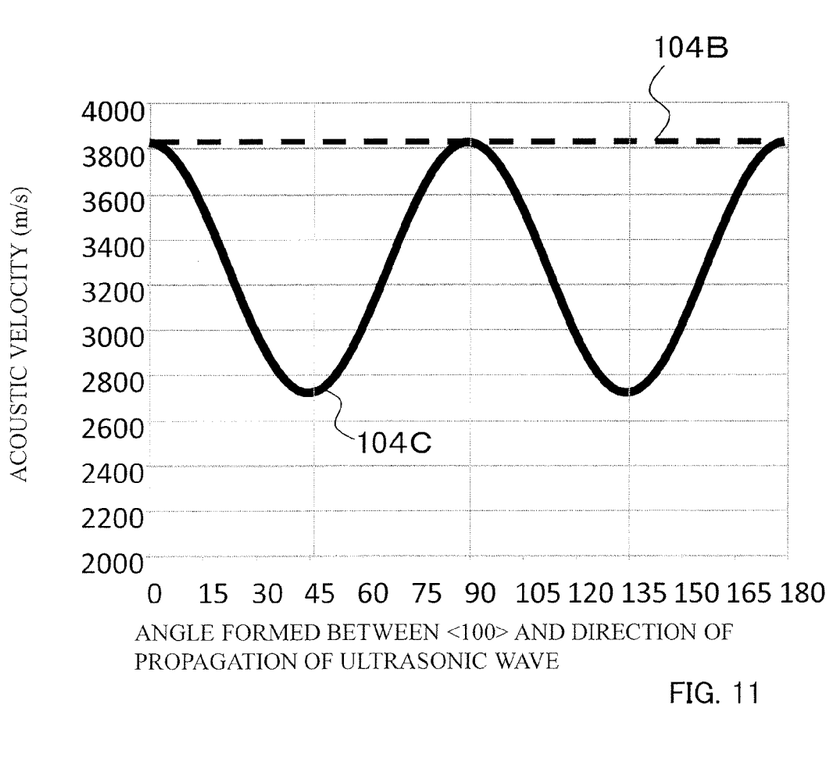
FIG. 11 is a diagram illustrating the measurement principle of the ultrasonic testing method according to the second embodiment of the present invention.

FIGS. 10 and 11 are diagrams illustrating the measurement principle of the ultrasonic testing method according to the second embodiment of the present invention.

As illustrated in FIG. 10, when an ultrasonic wave is incident on a material (such as a directionally-solidified material) having acoustic anisotropy, the ultrasonic wave propagates as three types of ultrasonic waves that have polarizations (or vibration direction) in directions that are perpendicular to each other in general.

The first one of the three waves is a wave 104D that vibrates in a direction nearly parallel to the propagation direction 104. The first wave 104D is treated as a longitudinal wave in general. When the first wave is distinguished from a longitudinal wave, the first wave is called a quasi longitudinal wave in some cases.

The second and third waves of the three waves have polarizations (or vibration direction) in directions that are perpendicular to the direction in which the quasi longitudinal wave vibrates. Thus, the second and third waves vibrate in the directions that are nearly parallel to a direction perpendicular to the propagation direction 104. It is not possible to physically distinguish the second and third waves if the second and third waves propagate in an isotropic medium. The second and third waves are called transverse waves. When an anisotropic medium is used, two types of transverse waves exist which have polarizations (or vibration direction) in directions perpendicular to each other. The vibration directions of the two types of the transverse waves 104B and 104C are different. In addition, acoustic velocities of the transverse waves 104B and 104C that propagate are different from each other.

FIG. 11 illustrates acoustic velocities of the transverse waves 104B and 104C which propagate in a single-crystalline material that is an ideal anisotropic material. For calculations illustrated in FIG. 11, the material is nickel base metal; the direction 104 in which the ultrasonic wave propagates matches a crystal orientation <100> (direction [100] in the example illustrated in FIG. 10); the direction (direction [001] in the example illustrated in FIG. 10) in which the first transverse wave 104C vibrates is parallel to the crystal orientation <100>; and the direction (direction [010] in the example illustrated in FIG. 10) in which the second transverse wave 104B vibrates is perpendicular to the crystal orientation <100>.

In the directionally-solidified material, crystal growth directions are averagely the direction <100> (direction [010]) in FIGS. 2 and 10). The directionally-solidified material is constituted by a polycrystalline material. Thus, the directionally-solidified material does not become an ideal state, unlike a single-crystalline material. In addition, it is difficult to accurately estimate the crystal orientations of the crystal grains that form the directionally-solidified material.

In the present embodiment, among ultrasonic waves to be received, an ultrasonic wave that propagates for a short time period is focused. The time period for the propagation is treated as a time period for the propagation in the test object. This is due to the fact that in an ideal state illustrated in FIG. 11, an acoustic velocity of the second transverse wave 104B is constant regardless of an angle formed between the direction <100> (direction [100] in FIG. 1) and the direction of the propagation of the ultrasonic wave and is always higher than that of the first transverse wave 104C that has dependence on an angle formed between the direction <100> (direction [100] in FIG. 1) and the direction of the propagation of the ultrasonic wave.

In this method, even when the crystal orientation <100> (direction [100] illustrated in FIG. 10) of crystal grains that form the test object is not known, the received signal 106B of the second transverse wave 104B that propagates for a shorter time period than the first transverse wave 104C is focused among the received signals 106B and 106C, and the difference between the time period for the propagation of the signal 106B and a time period for propagation of the signal 106A reflected from the top surface 101A of the test object is measured and treated as the time period T1 for the propagation. In this manner, the thickness of the test object can be measured.

In the present embodiment, the acoustic velocity of the second transverse wave 104B that has the polarization (or vibration direction) in the direction and propagates at the high velocity (illustrated in FIG. 11) is used as the velocity of the ultrasonic wave that is used to measure the thickness of the test object on the basis of the time period for the propagation.

In the present embodiment, the test object is the directionally-solidified material as described above. Even when the crystal orientations perpendicular to the crystal growth direction are random, the thickness of the test object can be measured using the time period for the propagation of the transverse wave and the acoustic velocity of the transverse wave.

In this case, the transverse wave is among the transverse ultrasonic waves, has the polarization (or vibration direction) in the direction and propagates for a shorter time period.

Next, details of an ultrasonic testing method according to a third embodiment of the present invention are described with reference to FIGS. 12 to 14B.

First, the configuration of an ultrasonic testing device that is used for the ultrasonic testing method according to the present embodiment is described with reference to FIG. 12.

Figure 12:
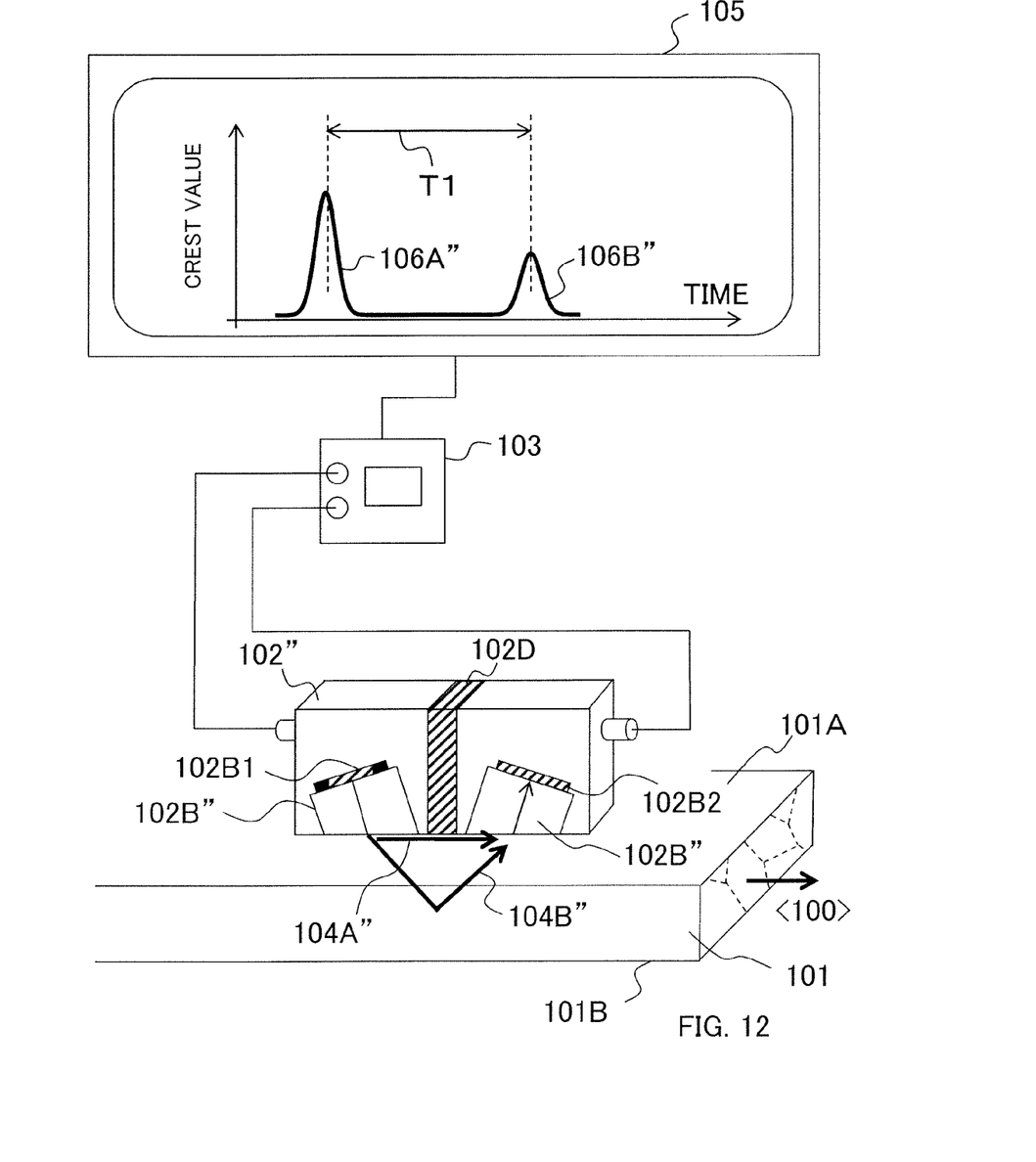
FIG. 12 is a diagram illustrating the configuration of an ultrasonic testing device that is used for an ultrasonic testing method according to a third embodiment of the present invention.

FIG. 12 is a diagram illustrating the configuration of the ultrasonic testing device that is used for the ultrasonic testing method according to the third embodiment of the present invention. In FIG. 12, reference numerals that are the same as those in FIG. 1 indicate the same parts.

In the present embodiment, an oblique incidence type longitudinal wave probe 102" is used. Other configurations are the same as those in FIG. 1. In order to cause an ultrasonic wave to be incident on the test object 101 in an oblique direction from the top surface 101A of the test object 101, the oblique incidence type longitudinal wave probe 102" has a buffer 102B".

The oblique incidence type longitudinal wave probe 102" is provided on the top surface 101A of the test object 101. The oblique incidence type longitudinal wave probe 102" includes a piezoelectric transducer 102B1 for transmission and a piezoelectric transducer 102B2 for reception. The oblique incidence type longitudinal wave probe 102" also has a sound insulating member 102D (such as a cork) between the piezoelectric transducer 102B1 for transmission and the piezoelectric transducer 102B2 for reception. The piezoelectric transducer 102B1 for transmission generates a longitudinal ultrasonic wave. The buffer 102B" refracts the generated longitudinal ultrasonic wave. Then, the oblique incidence type longitudinal wave probe 102" causes the longitudinal ultrasonic wave to propagate in an oblique direction in the test object 101. A longitudinal ultrasonic wave 104B" is reflected from the bottom surface 101B of the test object 101. The longitudinal ultrasonic wave 104B" is then received by the piezoelectric transducer 102B2 for reception and transmitted as a signal to the ultrasonic detector 103. The piezoelectric transducer 102B2 for reception receives an ultrasonic wave component 104A" that has directly propagated from the transmitting side to the receiving side, in addition to the longitudinal ultrasonic wave 104B" as described above.

Then, the thickness of the test object is evaluated on the basis of the difference T1 between a time period for propagation of a direct component 106A" directly propagating from the transmitting side to the receiving side and a time period for propagation of a component 106B" reflected from the bottom surface 101B of the test object 101. A crystal orientation <100> illustrated in FIG. 12 is the crystal growth direction.

Next, a measurement principle of the ultrasonic testing method according to the present embodiment is described with reference to FIGS. 13A and 13B.

Figure 13A:
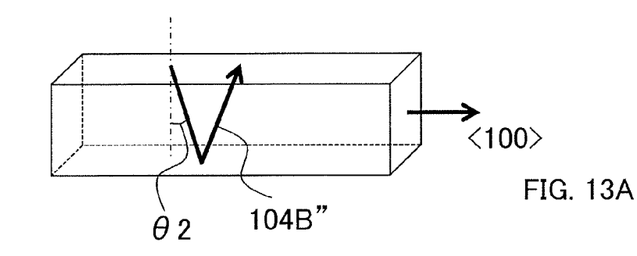
FIGS. 13A and 13B are diagrams illustrating a measurement principle of the ultrasonic testing method according to the third embodiment of the present invention.
Figure 13B:
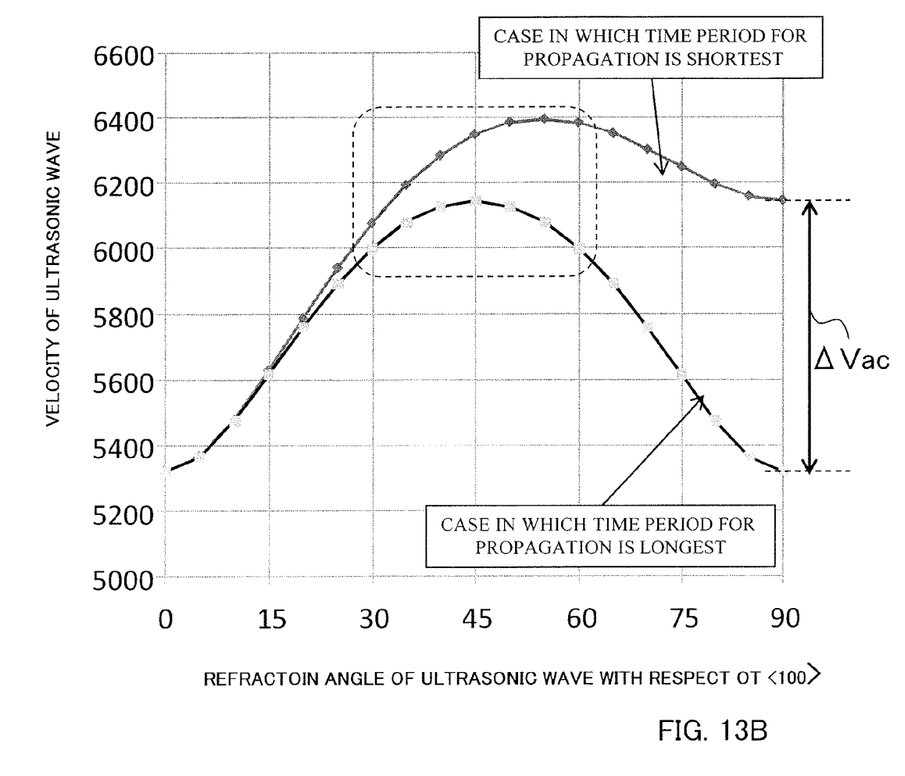

FIGS. 13A and 13B are diagrams illustrating the measurement principle of the ultrasonic testing method according to the third embodiment of the present invention.

As illustrated in FIG. 13A, a direction in which an ultrasonic wave propagates is indicated by 104B". In this case, a probe for transmission and a probe for reception are arranged side by side in a direction parallel to the crystal orientation <100> that is the crystal growth direction. An angle that is formed between the direction 104B" of the propagation of the ultrasonic wave and a direction perpendicular to the surface of the test object is indicated by θ2.

FIG. 13B illustrates an acoustic velocity of a longitudinal wave that propagates in an oblique direction in a material (such as a directionally-solidified material) having acoustic anisotropy. For calculations illustrated in FIG. 13B, the material is nickel base metal; and the probe for transmission and the probe for reception are placed side by side in the direction parallel to the crystal orientation <100>. In FIG. 13B, the angle θ2 that is formed between the direction 104B" of the propagation of the ultrasonic wave and the direction perpendicular to the surface of the test object is plotted along the abscissa, while the velocity of the longitudinal ultrasonic wave is plotted along the ordinate. In consideration of an effect of randomness of orientations (directions [100] and [001] illustrated in FIG. 2) perpendicular to the crystal growth direction <100>, the velocity of the longitudinal ultrasonic wave is calculated in each of the following two cases. In one of the two cases, the velocity of the longitudinal ultrasonic wave is the maximum (the time period for the propagation is the shortest). In the other case, the velocity of the longitudinal ultrasonic wave is the minimum (the time period for the propagation is the longest). For example, the velocity of the longitudinal ultrasonic wave is low when the longitudinal ultrasonic wave propagates in the crystal grain 301 illustrated in FIG. 3 (A). The velocity of the longitudinal ultrasonic wave is high when the longitudinal ultrasonic wave propagates in the crystal grain 302 illustrated in FIG. 3 (B).

When the vertical incidence type longitudinal ultrasonic wave probe illustrated in FIG. 1 is used, the relationship between a direction of propagation of an ultrasonic wave and the direction perpendicular to the surface of the test object corresponds to the case in which the angle θ2 plotted along the abscissa is 90 degrees, as shown in FIG. 13B. In this case, the difference Mac between the maximum of the velocity of the longitudinal ultrasonic wave and the minimum of the velocity of the longitudinal ultrasonic wave is the maximum. The measurement method using the vertical incidence type longitudinal ultrasonic wave probe is most easily affected by the randomness of the crystal orientations. This challenge is overcome by the present embodiment.

In the present embodiment, oblique incidence type longitudinal ultrasonic wave probes are disposed side by side in the crystal growth direction and face the test object so that the angle θ2 that is formed between the direction 104B" of the propagation of the ultrasonic wave and the direction perpendicular to the surface of the test object is in a range of approximately 30 degrees to 60 degrees.

In this case, the difference (calculated in consideration of an effect of the randomness of the orientation perpendicular to the crystal growth direction <100> (direction [010] illustrated in FIG. 2) between the maximum of the velocity of the ultrasonic wave and the minimum of the velocity of the ultrasonic wave is small compared to the case in which the vertical incidence type longitudinal ultrasonic wave probe is used (the angle θ2 plotted along the abscissa in FIG. 13B is 90 degrees). Thus, when the oblique incidence type longitudinal ultrasonic wave probes are used, the effect of the randomness of the crystal orientations can be reduced and the measurement can be performed with higher accuracy.

When the angle θ2 is in the range (indicated by a dotted rectangle illustrated in FIG. 13B) of approximately 30 degrees to 60 degrees, the velocity of the ultrasonic wave is a local maximum value. Thus, the amount of change in the velocity of the ultrasonic wave with respect to change in the angle θ2 is small compared to another angular range. The angle θ2 is an angle that changes according to the thickness of the test object. Thus, even when the thickness of the test object to be measured is not known, an effect of randomness of a crystal orientation can be reduced.

As the velocity of the ultrasonic wave or the average acoustic velocity of the ultrasonic wave corresponding to the range (of approximately 30 degrees to 60 degrees) in which change in the acoustic velocity is constant, the acoustic velocity of the ultrasonic wave propagating in the direction <110>, or the average velocity of the maximum and minimum acoustic velocities corresponding to the angle (plotted along the abscissa in FIG. 13B) of 45 degrees, is used.

Next, a method for calculating the thickness of the test object in the ultrasonic testing method according to the present embodiment is described with reference to FIG. 14.

Figure 14A:
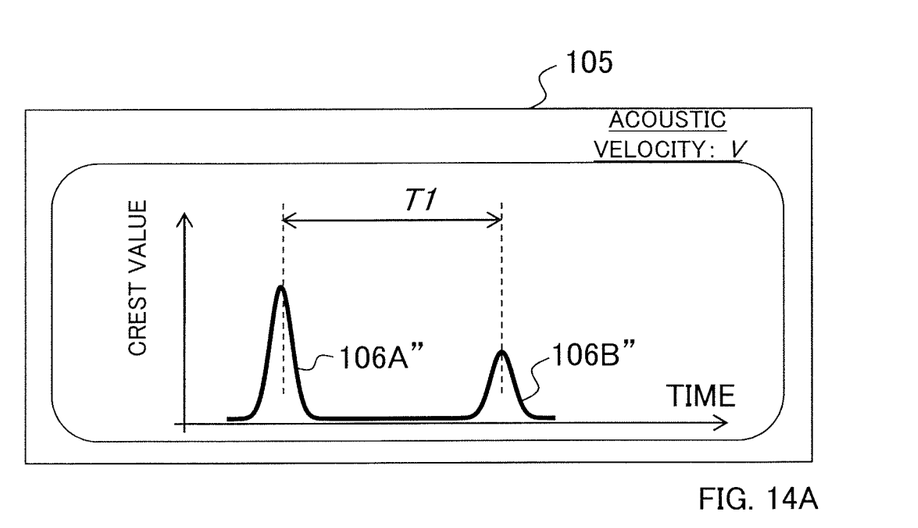
FIGS. 14A and 14B are diagrams explaining a method for calculating a thickness in the ultrasonic testing method according to the third embodiment of the present invention.
Figure 14B:
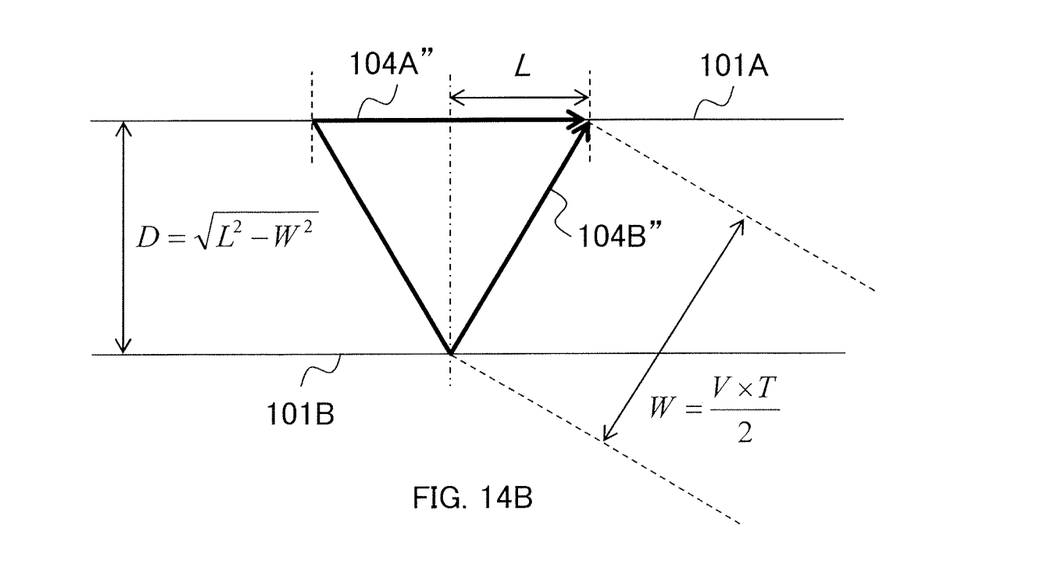

FIG. 14 is a diagram illustrating the method for calculating the thickness of the test object in the ultrasonic testing method according to the third embodiment of the present invention.

The difference T1 between a time period for propagation of the direct signal 104A" received by the oblique incidence type longitudinal ultrasonic wave probe and a time period for propagation of the reflected component 104B" is multiplied by an acoustic velocity V. Then, the value obtained by the multiplication is divided by 2. Thus, the distance W (=(V× T)/2) of the one-way propagation path is calculated.

A half of a distance between the probe for transmission and the probe for reception is indicated by L. Since the value L is determined by the arrangement of the probes, the value L is known before the measurement.

The depth D (thickness) can be calculated as a value of $\sqrt{(L^2-W^2)}$ from the value L (that is the half of the distance between the probes) and the distance W of the one-way propagation path according to the Pythagorean theorem.

According to the present embodiment, even when the test object is the directionally-solidified material and the crystal orientations that are perpendicular to the crystal growth direction are random, it is possible to reduce the effect of the randomness of the crystal orientations and measure the thickness of the test object by causing a longitudinal ultrasonic wave to propagate in an oblique direction.

What is claimed is:

1. An ultrasonic testing method, the method comprising the steps of:
    causing a transverse ultrasonic wave to be incident on a test object that has acoustic anisotropy and is constituted by a crystal structure, in a direction perpendicular to a surface of the test object; and
    measuring a thickness of the test object on the basis of a velocity of the transverse ultrasonic wave propagating in the test object and a time period for the propagation of the transverse ultrasonic wave, while using, as the time period for the propagation of the transverse ultrasonic wave, a time period for propagation of a transverse wave component that propagates in the test object for the shortest time period, among a plurality of transverse wave components that are obtained by dividing the transverse ultrasonic wave and have polarizations in the different directions (vibration direction) due to the acoustic anisotropy.

2. The ultrasonic testing method according to claim 1, wherein as the velocity of the transverse ultrasonic wave, a velocity of a transverse ultrasonic wave is used which is higher than that of the other transverse ultrasonic wave, the transverse ultrasonic wave being among transverse ultrasonic waves that propagate in a direction of a crystal orientation <100> and have polarizations in two directions.

* * * * *